US012092628B1

(12) United States Patent
Blanchard et al.

(10) Patent No.: US 12,092,628 B1
(45) Date of Patent: Sep. 17, 2024

(54) RESIN GEL-TIME TEST FIXTURE

(71) Applicant: The United States of America as represented by the Secretary of the Navy, Newport, RI (US)

(72) Inventors: Monica L Blanchard, South Kingstown, RI (US); Rachel E Blanchard, Cumberland, RI (US); Zachary R Golebieski, East Rutherford, NJ (US); James M LeBlanc, North Kingstown, RI (US); Thomas S Ramotowski, Tiverton, RI (US)

(73) Assignee: The United States of America as represented by the Secretary of the Navy

( * ) Notice: Subject to any disclaimer, the term of this patent is extended or adjusted under 35 U.S.C. 154(b) by 310 days.

(21) Appl. No.: 17/737,093

(22) Filed: May 5, 2022

(51) Int. Cl.
*G01N 33/44* (2006.01)
(52) U.S. Cl.
CPC .................................. *G01N 33/442* (2013.01)
(58) Field of Classification Search
CPC .................................................. G01N 33/442
See application file for complete search history.

(56) References Cited

U.S. PATENT DOCUMENTS

| 4,590,803 | A | * | 5/1986 | Harrold | G01N 29/032 |
| | | | | | 73/590 |
| 5,911,159 | A | * | 6/1999 | Choo | G10K 11/004 |
| | | | | | 73/632 |
| 10,689,978 | B2 | * | 6/2020 | Al-Sofi | G01N 33/24 |
| 11,614,391 | B1 | * | 3/2023 | Al-Sofi | E21B 43/16 |
| | | | | | 73/37 |

FOREIGN PATENT DOCUMENTS

| CN | 110631919 | A | * | 12/2019 | ............ G01N 3/10 |
| CN | 214844622 | U | * | 11/2021 | ............ G01N 11/10 |
| CN | 215263076 | U | * | 12/2021 | ............ G01N 19/04 |

* cited by examiner

*Primary Examiner* — Freddie Kirkland, III
(74) *Attorney, Agent, or Firm* — James M. Kasischke; Michael P. Stanley; Jeffry C. Severson

(57) ABSTRACT

A test fixture is provided with a pair of specimen molds. Each specimen mold includes a cylindrical specimen barrel with at least one open end with a guide rail attached to a bottom of the specimen barrel. The test fixture also includes a support body having a trough shaped to match the shape of the specimen barrel. A track is located at the bottom of the trough and extends the length of the trough. The specimen barrels are positioned in the support body having an open end of a first specimen barrel facing the open end of a second specimen barrel. The guide rail for each specimen barrel is positioned in the track at the bottom of the trough in the support body.

7 Claims, 3 Drawing Sheets

RESIN GEL-TIME TEST FIXTURE

STATEMENT OF GOVERNMENT INTEREST

The invention described herein was made in the performance of official duties by employees of the U.S. Department of the Navy and may be manufactured, used, or licensed by or for the Government of the United States for any governmental purpose without payment of any royalties thereon.

CROSS REFERENCE TO OTHER PATENT APPLICATIONS

None.

BACKGROUND OF THE INVENTION

1) Field of the Invention

The present invention is directed to a test fixture, and more particularly to a test fixture for holding specimens and evaluating the gel-times of epoxy-resin materials in a submerged environment.

2) Description of the Related Art

Due to their beneficial properties, including a comparatively high strength-to-weight ratio, a long operational life, and low maintenance costs; composite materials are utilized in numerous devices and equipment as well as used in a large range of applications. Composite materials have many desirable properties but are prone to damage due to impact events as well as normal operations due to cyclic loading. The presence of damage which evolves from operation has the potential to adversely and permanently affect operational capabilities and shock survivability.

Additionally, the nucleation and growth of inter-laminar and trans-laminar cracks due to thermal expansion and contraction cycles, thermal expansion mismatch of the fiber and matrix materials, and hygrothermal swelling may reduce in-situ structural survivability levels necessary to resist underwater explosion, shock, impact and implosion.

However, composites are highly susceptible to damaging cracks or tears within the matrix of the structure; thereby, leading to a substantive decrease in the material strength. This is especially true in an undersea environment due to high pressures at deep ocean depths, shock events, as well as contact with foreign objects. For composite structures designated as critical, these damage sites can lead to adverse consequences and can potentially degrade sensor performance due to forming of micro-cracks deep within the polymer matrix.

However, composites are used in components cannot be easily repaired while submerged. These damage sites are often difficult and expensive to repair in a submerged environment.

The ability to repair such damage while leaving the composite component in the water can provide significant reductions in cost and reductions in the time of return to service. Additionally, with the capability to repair small damage states while submerged in water; the ability for at-sea repairs becomes a viable option.

Many composites have a matrix comprised of a two-part epoxy/resin system. An important factor when selecting a resin system for the self-healing system and matrix of the composite is the gel and cure time of the proposed material in various environments.

To ensure that resins used in the repair of composite structures can appropriately gel and cure in submerged applications (or undersea environments); such resins must be tested. Optimally, such testing is performed in the environment in which the resin is to be applied.

Previous studies have investigated the effects of fracture, impact damage, and corrosion on self-healing composite materials, and its subsequent ability to autonomously itself in air. Previous studies have also developed methods for fabricating and evaluating self-healing epoxy/resin composites in dry applications (air). However, methods for fabricating and testing self-healing materials in marine environments has not yet been performed. A test method and fixture has not yet been developed to enable evaluation of candidate resin systems for undersea material repair.

Therefore, a fixture is required to test the gel and cure times of different materials in a baseline and underwater environment. The ability to quickly and reliably test a large number of resin combinations also ensures optimal material selection for undersea repair applications.

SUMMARY OF THE INVENTION

The primary object and general purpose of the present invention is to provide a test fixture for conducting gel-time testing of two-part resin systems in submerged environments.

It is a further objective of the present invention to provide a test fixture to measure the effectiveness of a two-part resin system in a submerged environment, while also conducting the testing in a controlled laboratory setting.

A test fixture is provided for testing the gel time and cure times of two-part resin systems for use in submerged environments. The test fixture includes a support body and a pair of specimen molds. Each specimen mold holds one part of the resin system. Each specimen mold and has one open end, and a bottom guide rail to maintain an alignment with the support body. The two specimen molds are positioned in the support body, with their open ends facing each other.

These and other objects, features, and advantages of the present invention will become more readily apparent from the attached drawings and the detailed description of the invention.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

The present invention provides a test fixture that can quantify gel time of a two-part epoxy-resin system in air, fresh water, and salt water over a wide range of temperatures corresponding to specific environments. This gel time data can then be used in the selection of an optimized repair system.

The test fixture enables the evaluation of a repair system that facilitates underwater repair of composite damage through a resin that cures quickly and effectively underwater. The identification of a resin through controlled laboratory testing that is able to perform underwater repairs for minor damage of composite marine components is a significant benefit, as it prevents the need to remove and dry damaged components from the water prior to repair.

The test fixture includes two components that allow the constituent materials of a two-part epoxy-resin system to align and gel in a variety of dry or submerged environments. During use, the gel-time is recorded and the gel-time data is used to compare various epoxy-resin systems and thereby inform the design process for a wetted composite structure.

Figure 1:
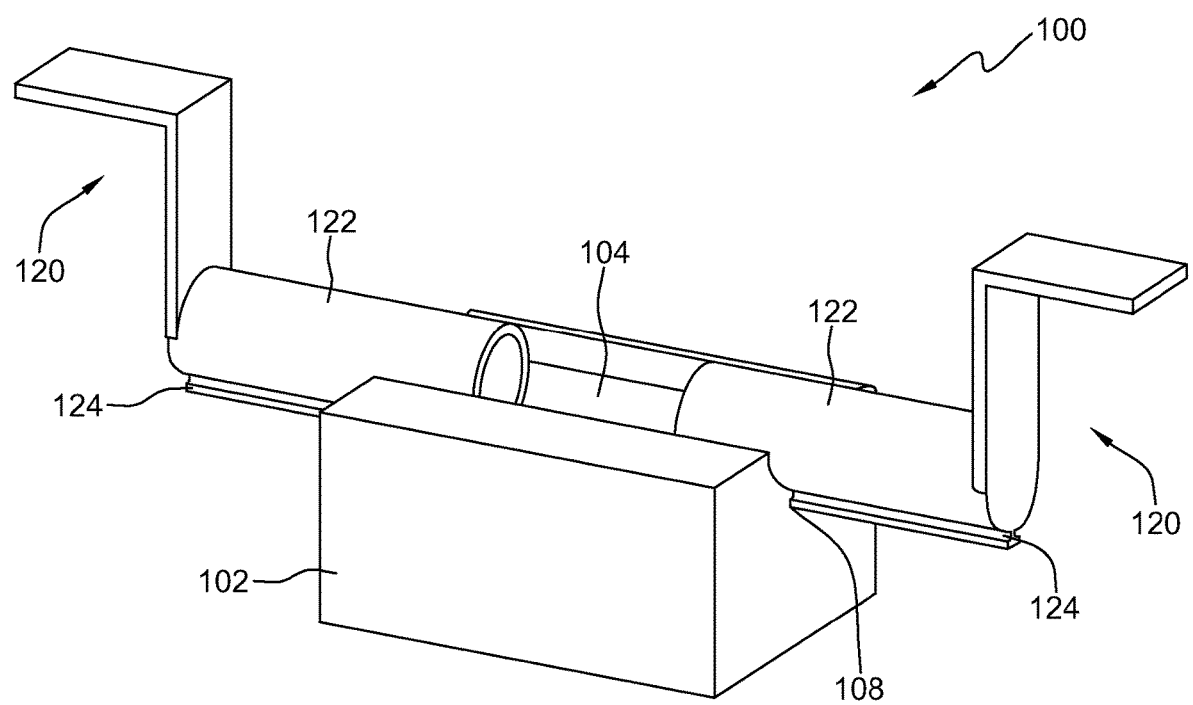
FIG. 1 is a perspective view of a test fixture according to the present invention.

Referring now to the drawings, FIG. 1 depicts a test fixture 100 with a support body 102 and a trough 104 located in the support body. The concave profile of the trough 104 aligns with the cylindrical profile of specimen barrels 122, to allow the specimen barrels to move axially within a support track 108.

Figure 2:
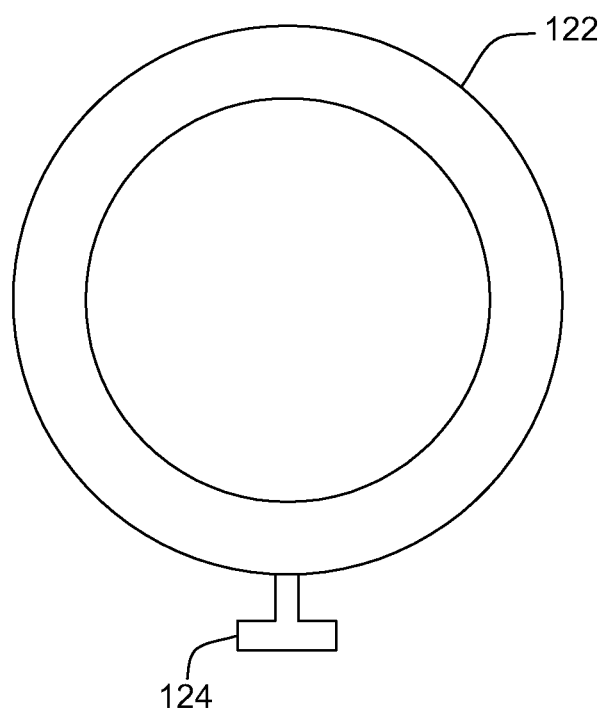
FIG. 2 is a cross-section view of the specimen mold.

The support track 108 is provided along the bottom length of the trough 104. The support track 108 is a keyhole slot for a guide rail 124 of the specimen barrel 122 (See FIG. 2).

Figure 3:
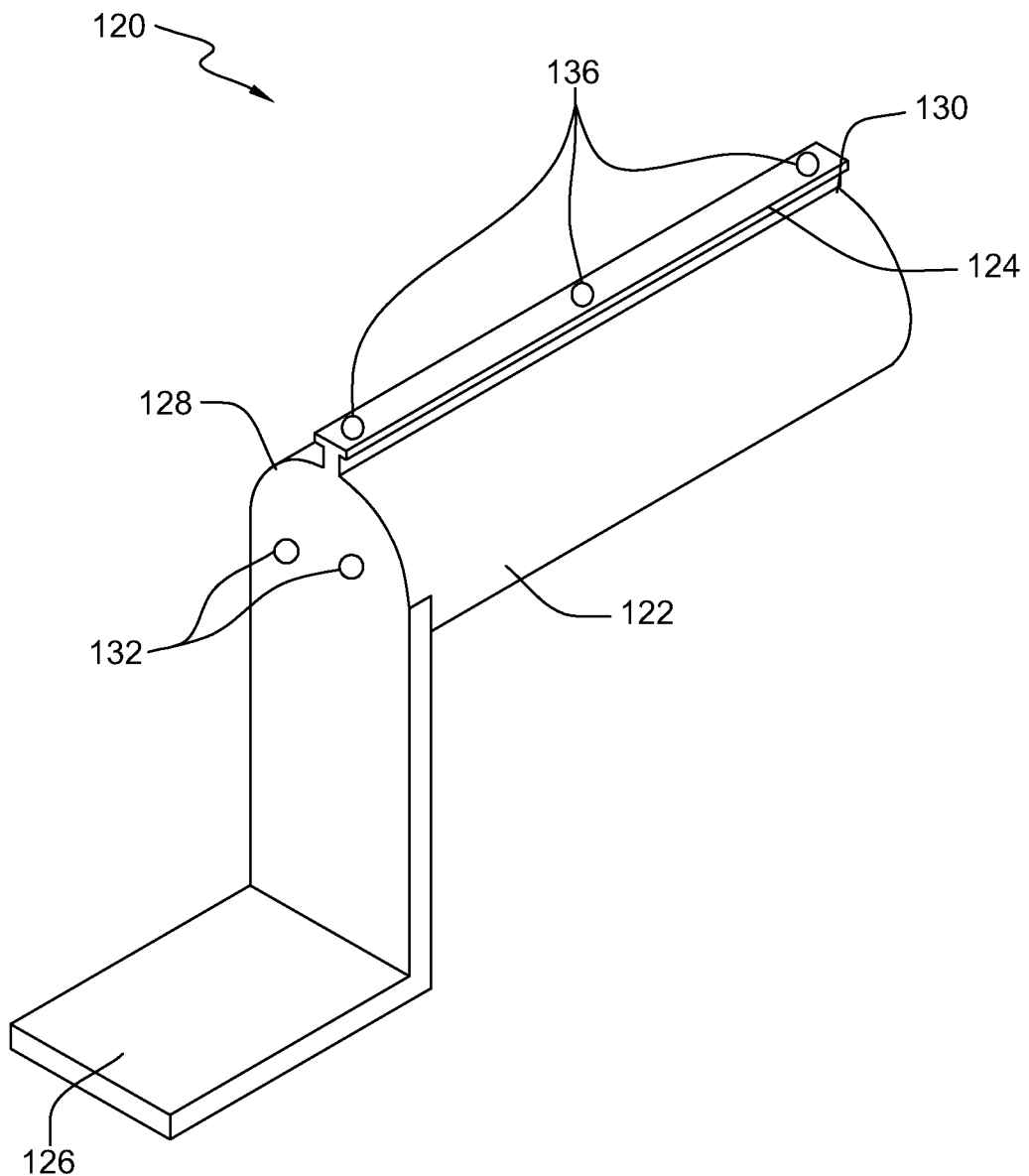
FIG. 3 is a perspective view of a specimen mold according to the present invention with the mold viewed upside down to show the guide rail.

FIG. 3 depicts a specimen mold 120 with the specimen barrel 122, a handle 126 and the guide rail 124. The specimen barrel 122 is a cylinder having a closed first end 128 and an open second end 130. The L-shaped handle 126 attaches to the first end 128 by fasteners 132. The guide rail 124 attaches to the bottom of the specimen barrel 122 by fasteners 136. The test fixture 100 includes the two specimen molds 120 engaged with the support body 102 in such a way that maintains alignment of the resin samples within the two specimen molds.

In use, a resin sample is placed in the open end 130 of each of the two specimen barrels 122. The specimen barrels 122 are set in the trough 124 and the guide rail 124 is inserted in the support track 108. The specimen barrels 122 are slid axially along the support track 108 toward each other, until the faces of the two resin samples make contact. The test fixture 100 maintains alignment of the resin samples within the two specimen barrels 122. The alignment enabled by the test fixture 100 ensure complete contact between the faces of the two resin samples, which is critical for the success of the gel-time testing.

The gel-time testing is initiated by preparing the two-part (Part A & B) epoxy-resin system per the mixing ratio provided on a Technical Data Sheet for the testing. Each specimen barrel 122 is filled with the mixed epoxy-resin, creating a base layer. The base layer within each specimen barrel 122 is then allowed to cure for at least 12 hours.

The test fixture 120 has been successfully demonstrated to measure the gel time of the epoxy-resin systems under various dry and wetted conditions, including fresh and saltwater environments. The test fixture 100 provides the capability to evaluate in a controlled environment, the effectiveness of epoxy-resin systems for underwater repair of composite structures.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A test fixture for testing gel and cure times of two-part epoxy resin materials, said test fixture comprising of:
    a support body; and
    a pair of specimen barrels with a specimen holder having one open end and a guide rail affixed to said specimen barrel and aligned in a track in said support body;
    wherein said pair of specimen barrels when aligned in said support body have the open end of a first specimen mold facing the open end of a second specimen mold.

2. The test fixture of claim 1, wherein at least one of said specimen molds further includes a handle attached to an opposite end of said specimen holder.

3. The test fixture of claim 2, wherein said specimen holder is a cylindrical body.

4. The test fixture of claim 3, wherein said support body further comprises a trough shaped to accommodate a shape of said specimen holder.

5. The test fixture of claim 4, wherein a track is located at the bottom of the trough and extends the length of the trough.

6. The test fixture of claim 1, wherein said guide rail is T-shaped.

7. The test fixture of claim 6, wherein a length of the track is key-slotted to match said shaped guide rail.

* * * * *